United States Patent
Vergano et al.

[11] Patent Number: 5,845,643
[45] Date of Patent: Dec. 8, 1998

[54] ARM BOARD FOR VASCULAR ACCESS AND METHOD OF USING THE SAME

[75] Inventors: Egidia M. Vergano, Los Altos, Calif.; Joseph Kovacs, Cranston, R.I.

[73] Assignee: Dale Medical Products, Inc., Plainville, Mass.

[21] Appl. No.: 658,362

[22] Filed: Jun. 5, 1996

[51] Int. Cl.$^6$ .................................................. A61F 5/37
[52] U.S. Cl. .................................. 128/877; 128/DIG. 6; 602/21
[58] Field of Search .................................. 602/20, 21, 22; 128/877–879, 882, DIG. 15, DIG. 6

[56] References Cited

U.S. PATENT DOCUMENTS

| | | | |
|---|---|---|---|
| D. 323,216 | 1/1992 | Russell et al. | D24/190 |
| D. 340,524 | 10/1993 | Russell | D24/190 |
| 2,763,264 | 9/1956 | McInnerny | 128/214 |
| 3,256,880 | 6/1966 | Caypinar | 128/133 |
| 3,556,092 | 1/1971 | Eisenberg | 128/87 |
| 3,640,273 | 2/1972 | Ray | 128/87 |
| 4,286,588 | 9/1981 | Lovegrove | 128/133 |
| 4,862,904 | 9/1989 | West et al. | 128/877 |
| 4,928,712 | 5/1990 | Mill | 128/877 |
| 4,941,479 | 7/1990 | Russell et al. | 128/877 |
| 4,945,925 | 8/1990 | Garcia | 128/877 |
| 5,025,801 | 6/1991 | Callaway | 128/877 |
| 5,058,576 | 10/1991 | Grim et al. | 128/87 R |
| 5,370,346 | 12/1994 | Long | 248/118.5 |
| 5,417,645 | 5/1995 | Lemmen | 602/21 |
| 5,623,951 | 4/1997 | Kamaya | 128/877 |

OTHER PUBLICATIONS

"The Lundy Universal, A Unique Multipurpose Arm Board," Anesthesiology News, Jul. 1994.
GennyDenny® Arterial–Line Wrist Restraint, Developed by TADCO, Inc., Farmington, MA, 1992.
"Principles and Practice of Anesthesiology," Rogers, Tinker, Covino, Longine, vol. 1, pp. 760–764 (1993).
"Arterial Line Insertions," Anesthesiology News, Aug. 1995.
"Allen's Test" as described in published literature (Part VI, Specific Applications, FIG. 23.3, p. 482).
"Wrist/Hand Support With Removable Curved Steel Bar," Dale Medical Products, Inc., Jan. 1983.

*Primary Examiner*—Corrine M. McDermott
*Assistant Examiner*—Cris L. Rodriguez
*Attorney, Agent, or Firm*—Wolf, Greenfield & Sacks, P.C.

[57] ABSTRACT

An arm board and method of using the same for positioning and restraining the forearm and hand of a patient to receive either an intravenous or intra-arterial line. An elongated malleable core member is provided with padding on at least one surface, the core member having an adjustable bending point along the length with the member capable of nonpermanently bending at the bending point from a flat configuration to an angled configuration. A pair of adjustable straps secure the patient's hand and forearm to the core member.

16 Claims, 4 Drawing Sheets

ARM BOARD FOR VASCULAR ACCESS AND METHOD OF USING THE SAME

FIELD OF THE INVENTION

This invention relates generally to a disposable arm board and method for positioning and restraining the forearm and hand of a patient to receive either an intravenous or intra-arterial line.

BACKGROUND OF THE INVENTION

Intravenous and intra-arterial lines are used in hospitals and clinics for fluid administration, pressure monitoring, and as a port for obtaining blood specimens. Since these lines provide a variety of critical life functions, it is absolutely necessary that the lines are placed and held properly in the patient's artery or vein to avoid unnecessary punctures, tearing of the vein or artery, kinking of the fluid lines, instability or accidental dislodgement.

There are several known techniques for arterial catheter placement, also known as arterial cannulation. The key to proper radial arterial line insertion is maintaining the correct extension and flexion of the wrist. Since arteries are not as superficial (i.e., close to the skin) as veins, the correct extension of the wrist will lift and elevate the radial artery so that it is more stabilized in the tissue plane of the wrist and forearm. Once the radial artery has been raised by proper wrist flexion, the area surrounding the artery should be examined by gentle touching with two or three fingers to appreciate the pulsation. This technique prior to catheter insertion can avoid fluid flow problems.

The skin overlying the radial artery is very sensitive and the artery has a tendency to spasm as cannulation is made. Therefore, the wrist area needs to be restrained at the proper angle and flexion position to reduce the chance of improper insertion of the catheter due to the patient's voluntary or involuntary movements.

The catheter and needle combination are inserted at a 30° to 45° angle to the skin in the long plane of the artery (see FIG. 2). This insertion is done slowly and deliberately. During actual insertion, natural reflexes in the wrist area and spasms in the artery should be restrained.

The importance of maintaining optimum wrist position and avoiding catheter movement remains even after the catheter is in place. Wrist movements enhance the danger of decannulation of the intra-arterial line. This would cause the blood to flow out of the radial artery at systolic pressure, which could cause a person to bleed to death. The application of immediate pressure would be required to eliminate the occurrence of a large hematoma that would directly occlude the artery. To avoid this, the arterial line flange or adaptor is typically sewn to the skin to prevent the line from becoming dislodged. However, the need for additional securement and stability of the wrist position is necessary to prevent catheter movement in order to avoid tissue erosion of the artery.

Because of anatomical differences among individuals, the optimal wrist position is not the same for all patients. For example, a heavier patient arm needs to be hyperextended a greater amount in order to elevate the artery to the surface of the skin. Traditional methods of stabilizing the arm do not typically account for this, and therefore, the wrist may not be positioned in the ideal flexion position to receive an arterial line.

In the past, arm support boards and wrist restraints were often fabricated by the medical staff as needed. Numerous materials have been used, such as gauze, tape, or towels, to adjust and adapt the wrist of a particular individual to the proper position. Gauze or towels have been taped onto a straight board to obtain a suitable angle for the wrist (see FIG. 2). Other arterial line wrist restraints do not provide support or restraint for the wrist, allowing the patient to move and pull out from under the restraint and, thereby, risk decannulation of the line. Adhesive tapes are typically added to secure the wrist and conduits, but this has the disadvantage of painful removal from the patient and/or skin irritation. Various straps with different fasteners have also been employed, but none can be optimally employed to provide both intravenous and inter-arterial line placement and adjustment for individual anatomical differences.

SUMMARY OF THE INVENTION

An arm board is provided which supports and provides vascular access to a patient's wrist while receiving either an intravenous or intra-arterial line. The board is convenient to use, disposable, adjustable and easy to manufacture.

The board includes a malleable core member which has at least one padded surface and a user-determined, adjustable bending point along the board. The core member is capable of non-permanently bending at the adjustable bending point from a flat configuration to an angled configuration.

The core member is preferably enclosed by a cover and a pair of straps extend from the cover for fastening and securing a patient's forearm and hand in the proper position to receive an intravenous or intra-arterial line.

In use with an arterial line, the arm board is selectively bent by the user, preferably at a point approximately two-thirds the length of the board. In this angled configuration, the board is non-permanently bent at an angle of about 30° to about 45°. The patient's arm is placed on the padded side of the board with the palm facing up and positioned/repositioned by further adjusting the location or angle of the bend to provide optimal wrist position for easier and more accurate artery access and cannulation. The wrist, hand and arm are then stabilized by fastening straps across the palm (preferably including the thumb) and the lower forearm to eliminate catheter movement and provide easy access to the catheter site.

Alternatively, the arm board may be used in a flat configuration for supporting the arm, hand and wrist during intravenous feeding. The arm may be placed on the board in either a palm up or palm down position, and secured with straps across the wrist, forearm and/or hand.

DETAILED DESCRIPTION

Figure 1:
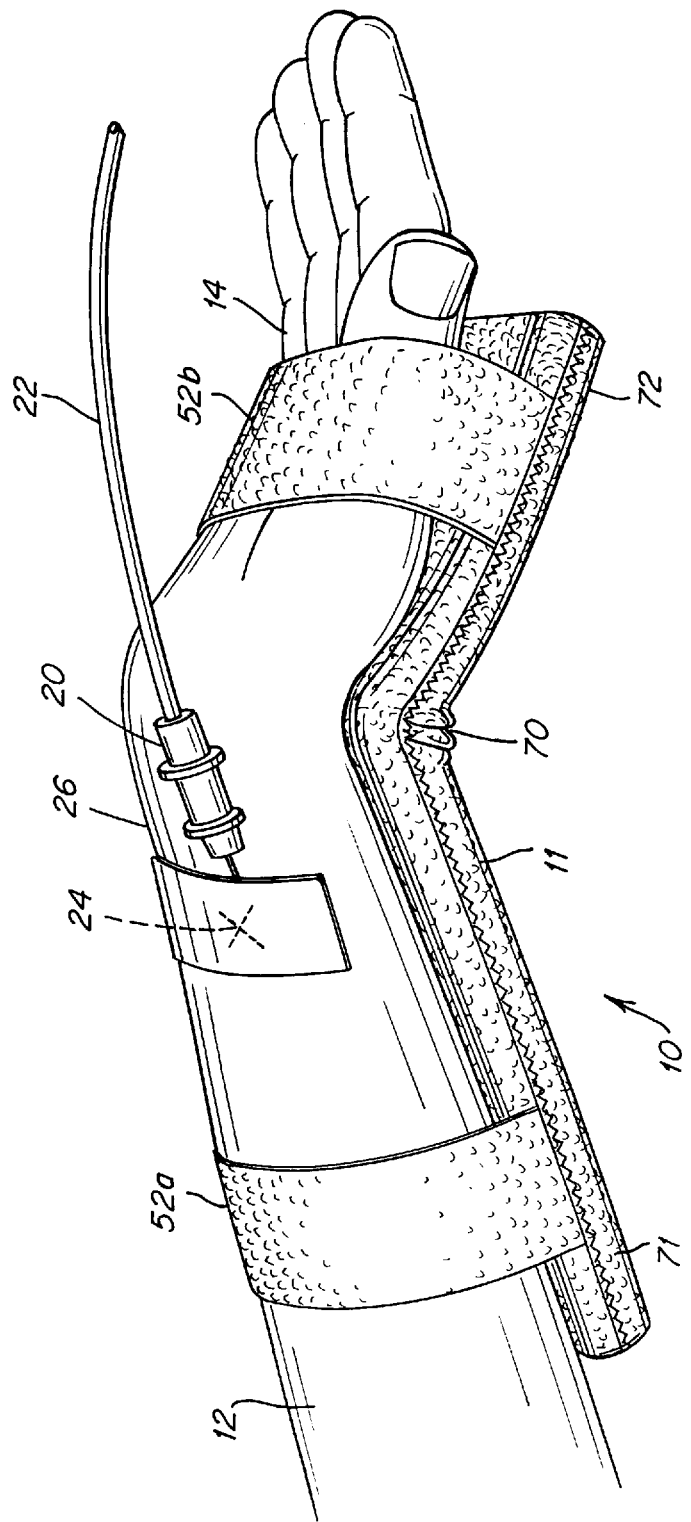
FIG. 1 is a top perspective view of an arm board of the present invention in use on a patient, for arterial line placement.

Referring to FIG. 1, one embodiment of an arm board 10 of the present invention is shown during use on a patient for arterial line placement. A padded elongated board member 11 is bent at an acute angle to provide the proper angle and wrist position for receiving an arterial line 22 and catheter 20. The patient's wrist 26 is positioned at the bend location 70 and the patient's forearm 12 and hand 14 (across the palm and including the thumb) are secured to the board portions 71, 72 on opposing sides of the bend 70 by a pair of straps 52a and 52b, respectively. In this manner, the patient's forearm 12 remains in the proper wrist flexion position as the catheter 20 is inserted into an entry site 24 on the wrist 26 and into the radial artery. The arm board 10 maintains the wrist position after insertion of the catheter 20 for the entire time of use and thereby aids in the prevention of decannulation and instability of the arterial line 22.

Figure 2:
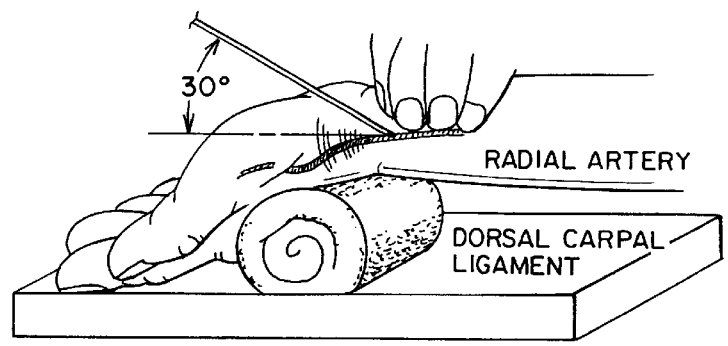
FIG. 2 is a side perspective view of a prior art method of flexing the wrist for receiving an intra-arterial line, using a flat board and a roll of gauze.

This avoids many of the problems associated with prior art methods of arterial catheter placement, as depicted in FIG. 2. A roll of gauze or a towel was placed under the patient's wrist, as shown, to achieve wrist flexion for access to the radial artery. The gauze or towel is soft and movable, and the hand and forearm may be unrestrained, thus increasing the risk of improper catheter placement and possible decannulation.

Figure 3:
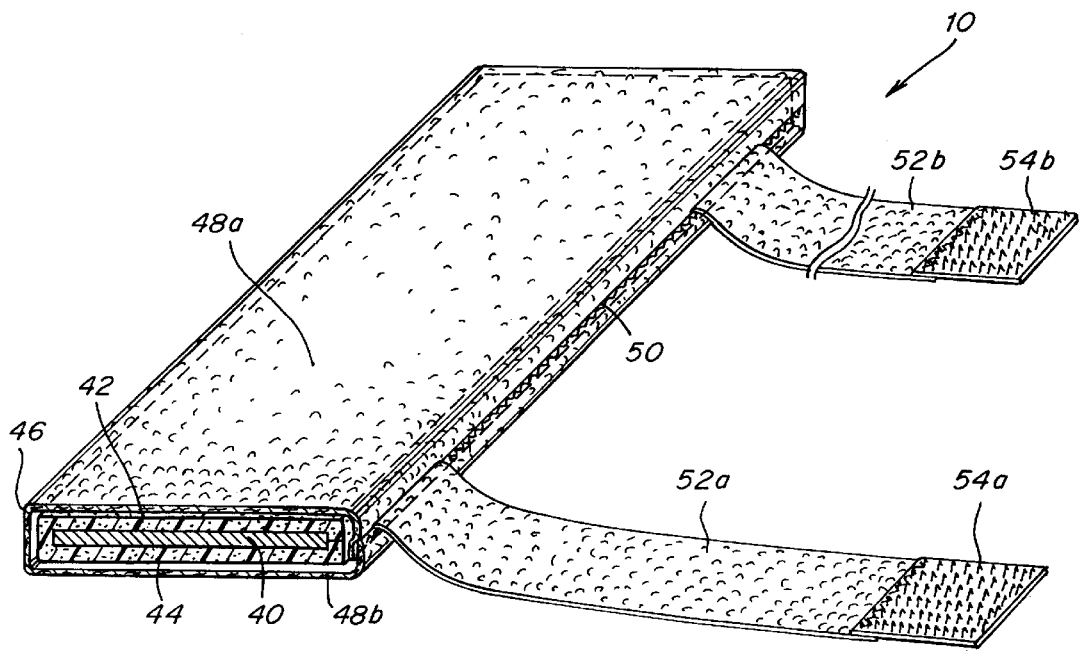
FIG. 3 is a vertical cross-section of the arm board of FIG. 1.

FIG. 3 is a cross section illustrating the construction of the disposable arm board. The arm board comprises a planar and generally rectangularly-shaped and malleable core member 40 which has upper and lower padded surfaces 42 and 44, and a cover or pocket 46 enclosing the same. The pocket is made of a flexible material and has a pair of upper surfaces 48a and 48b. One edge 50 of the pocket has two straps 52a and 52b extending transversely to the length of the board. The straps 52a and 52b each have an adjustable fastener 54a and 54b at a terminal end thereof. In this embodiment, the pocket is made of a nonwoven, stretchable, nonabsorbing material which is sewn along three edges; the material is available from International Paper, Veratec Division, Walpole, Mass. Such materials are commercially available and commonly used in surgical gowns, drapes, garment linings, diapers, etc. These materials are available as either absorbing or nonabsorbing materials, and both are suitable for use in this invention.

The malleable core member 40 has a user determined and adjustable bending point along the length of the board. The core member 40 and surrounding layers are capable of non-permanently bending at an adjustable bending point 70 from a flat configuration shown in FIG. 4, to an angled configuration shown in FIG. 6. The malleable core member 40 in this example is a 1/16 inch thick, 8½×3½ rectangular aluminum sheet, but any malleable material would be suitable. The upper and lower padded surfaces 42 and 44 are made from an adhesive-backed polyethylene foam sheet which is folded over and surrounds the malleable core member 40.

The straps 52a and 52b which extend from one edge 50 of the outer pocket are made of the same material as the cover. The straps 52a and 52b are capable of stretching lengthwise to provide a secure fit and restraint of the patient's arm and hand. Velcro-type fasteners 54a and 54b located on the end of each strap 52a and 52b enable adjustable positioning and repositioning of the arm board to the patient. In addition to hook and loop fasteners, the fasteners may include buckles, snaps or any other commonly known fastener.

Figure 6:
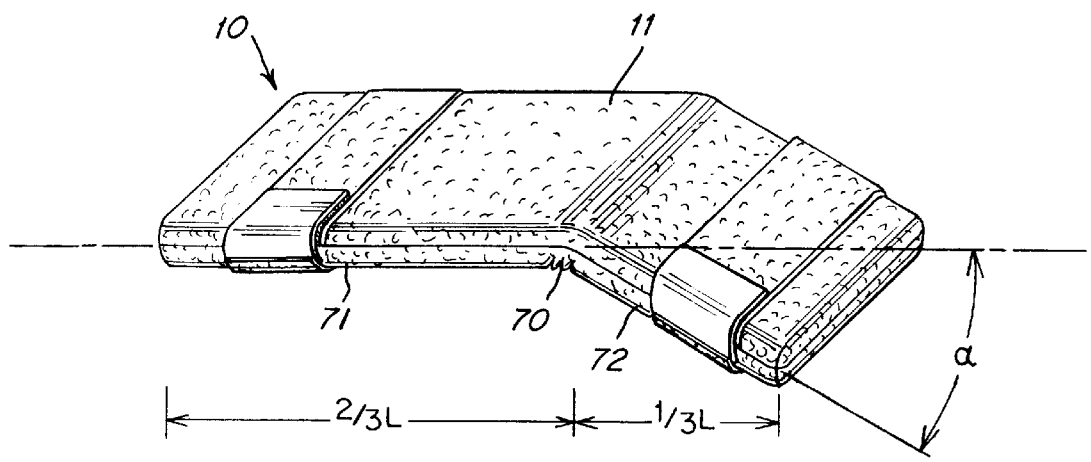
FIG. 6 is a perspective view of the arm board in an angled configuration.
Figure 7:
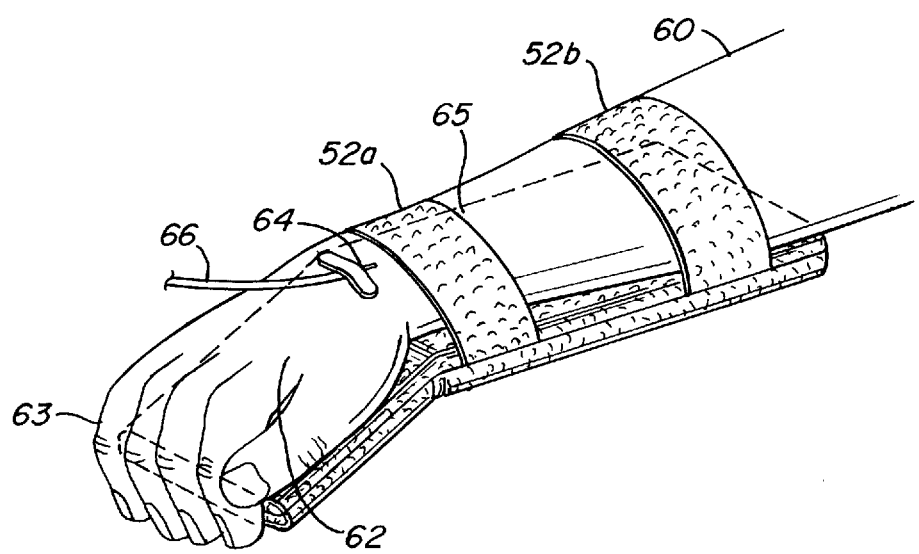
FIG. 7 is a perspective view of an arm board of the present invention in use on a patient for venous line placement, in an angled configuration.

Referring to FIGS. 1 and 6, the arm board 10 can be described for use during an arterial line placement. The board member 11 is selectively and nonpermanently bent at the adjustable bending line 70 to form a two-part angled configuration from a flat configuration. For optimal wrist flexion and artery access, the bending line 70 is located at a point approximately two-thirds the length L of the board member 11. Approximately one-third of the board (positionable under the hand) is non-permanently bent downward from the flat configuration at an angle a of about 30° to about 45°.

The patient's arm 12 is placed on the board member 11 with the palm facing upward. In this position, with the wrist flexed over the bending line 70, the radial artery is brought closer to the surface of the skin. The straps 52a and 52b are then stretched and wrapped snugly around the lower forearm and the palm area, respectively. The strap 52b may go over the thumb to ensure that it is restrained from movement. When the straps 52a and 52b have been stretched fully and wrapped tightly, the fasteners 54a, 54b will secure the straps.

The wrist 26 is now secured in proper position and ready to receive a radial arterial line 22 at the entry site 24 for the catheter 20; the entry site is located on the wrist 26, at a readily accessible space between the straps.

Figure 4:
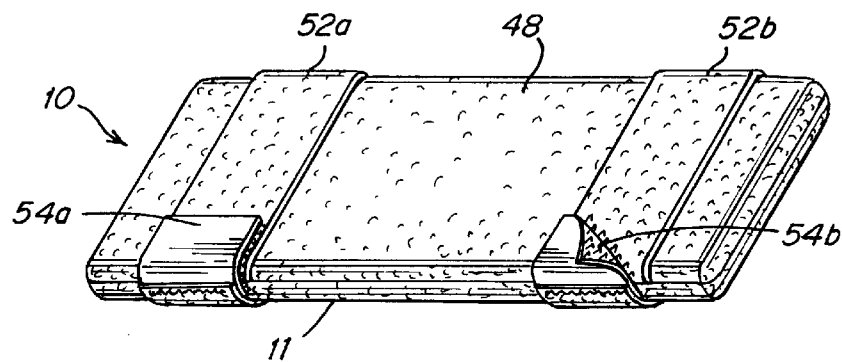
FIG. 4 is a top perspective view of the arm board in a flat configuration.
Figure 5:
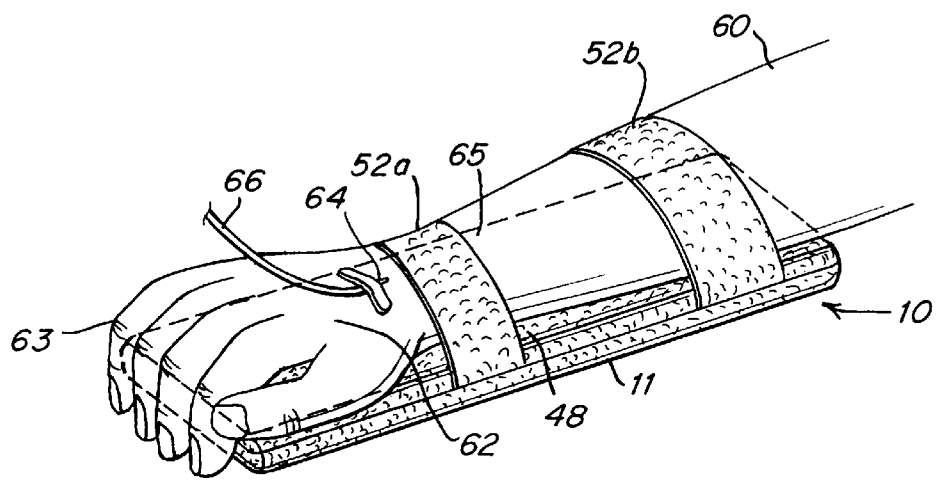
FIG. 5 is a perspective view of the arm board in use on a patient for venous line placement, in the flat configuration.

Referring to FIGS. 4 and 5, the flat configuration is shown for use as a support apparatus for the patient while receiving an intravenous line 66. The arm 60 is placed on the upper surface 48 of the board member 11 with the hand and palm 62 facing down; the fingers 63 may extend over the end of the board member. The straps 52a and 52b are extended and wrapped over the forearm 60 and wrist 65 (or hand) to secure them to the board member. The intravenous line 66 can be inserted at an entry site 64 in an area on the back of the hand, adjacent the wrist. In this application, one may optionally bend the end of the board member (under the hand) either up or down to accommodate a more natural resting hand or prone wrist position.

Further modifications including providing cover which is open at one end (as opposed to being sewn shut on all edges) to enable removal of the core member and replacement with a new cover. The cover may be adhered to the core member to prevent movement between the two components. Still further, the straps may be provided separately (not attached to) the core member.

Additional modifications of the invention described above will occur to those skilled in the art and are intended to be within the scope of the invention as defined by the claims.

We claim:

1. An arm board for positioning and restraining a patient's hand to receive an arterial line comprising:

an elongated malleable core member having a length and opposed upper and lower surfaces with at least the upper surface being padded, the core member having an adjustable bending point along the length with the core member capable of non-permanently bending at the bending point from a flat configuration to an angled configuration and having a width sufficient to support both the patient's wrist and hand at a suitable angle of flexion to receive the arterial line; and at least one strap positionable around the core member and engageable with at least one of the patient's hand or forearm in order to secure the patient's hand or forearm, wherein the patient's forearm and hand are positionable, palm up, on the upper padded surface with the patient's wrist flexed at the bending point and the artery being accessible for receiving the arterial line, when the at least one strap secures the at least one of the patient's hand and forearm to the arm board.

2. The arm board of claim 1, further including:

a cover enclosing the malleable core member and padded surface, with the straps extending from the cover.

3. The arm board of claim 2, wherein the cover is made of an absorbing material.

4. The arm board of claim 2, wherein the cover is made of a nonabsorbing material.

5. The arm board of claim 1, wherein the core member in the angled configuration is bent at an angle of about 30° to about 45°.

6. The arm board of claim 1, wherein the bending point is located at about two-thirds of the length of the core member.

7. The arm board of claim 1, wherein the padded surface comprises a foam material.

8. The arm board of claim 1, wherein the malleable core member is made of aluminum.

9. The arm board of claim 1, wherein the straps are stretchable.

10. The arm board of claim 1, wherein the straps have hook and loop fasteners.

11. The arm board of claim 1, wherein both the upper and lower surfaces are padded.

12. The arm board of claim 1, wherein the core member is in the flat configuration and a patient's forearm and hand are positionable, palm down, on the upper padded surface for receiving an intravenous line, with the patient's fingers flexed at the bending point.

13. An arm board for positioning and restraining a patient's hand to receive an intravenous line comprising:

an elongated malleable core member having a length and opposed upper and lower surfaces with at least the upper surface being padded, the core member having an adjustable bending point along the length with the core member capable of non-permanently bending at the bending point from a flat configuration to an angled configuration and having a width sufficient to support both the patient's wrist and hand at a suitable angle of flexion to receive the intravenous line; and at least one strap positionable around the core member and engageable with at least one of the patient's hand or forearm in order to secure the patient's hand or forearm, wherein the patient's forearm and hand are positionable, palm down, on the upper padded surface with the patient's fingers flexed at the bending point and a back portion of the patient's hand being accessible for receiving the intravenous line, when the at least one strap secures the at least one of the patient's hand and forearm to the arm board.

14. A method of securing a patient's forearm and hand to an arm board in a variety of use positions comprising:

providing an elongated malleable core member having a length and opposed upper and lower surfaces with at least the upper surface being padded, the core member having an adjustable bending point along the length with the core member capable of non-permanently bending at the bending point from a flat configuration to an angled configuration and having a width sufficient to support both the patient's wrist and hand at a suitable angle of flexion to receive the arterial line;

securing at least one of the patient's forearm and hand to the arm board with at least one adjustable strap positionable around the core member;

wherein in a first use, the core member is in the angled configuration and the patient's forearm and hand are positionable, palm up, on the upper padded surface with the patient's wrist flexed at the bending point for receiving an arterial line.

15. The method of claim 14, wherein in a second use, the core member is in the angled configuration and a patient's forearm and hand are positionable, palm down, on the upper padded surface for receiving an intravenous line, with the patient's fingers flexed at the bending point, and the straps securing the patient's hand and forearm to the arm board.

16. The method of claim 14, wherein in a third use, the core member is in the flat configuration and a patient's forearm and hand are positionable, palm down, on the upper padded surface for receiving an intravenous line, and the straps secure the patient's hand and forearm to the arm board.

* * * * *